United States Patent [19]

Miller et al.

[11] Patent Number: 5,068,478

[45] Date of Patent: Nov. 26, 1991

[54] PRODUCING ALKENES AND ALKYNES FROM ALKANES AND ALKENES

[75] Inventors: Jorge Miller; Miguel Kling, both of Bogota, Colombia

[73] Assignee: Energia Andina, Ltd., Bogota, Colombia

[21] Appl. No.: 528,603

[22] Filed: May 25, 1990

[51] Int. Cl.[5] ............................................... C07C 1/00
[52] U.S. Cl. .................................... 585/324; 422/188; 585/642
[58] Field of Search ................ 585/324, 642; 422/188

[56] References Cited

U.S. PATENT DOCUMENTS

| | | | |
|---|---|---|---|
| 2,320,274 | 5/1943 | Gorin | 585/322 |
| 2,488,083 | 11/1949 | Gorin et al. | 585/642 |
| 4,579,996 | 4/1986 | Fontfreide et al. | 585/642 |
| 4,665,270 | 5/1987 | Brophy et al. | 585/642 |
| 4,795,843 | 1/1989 | Imai et al. | 585/642 |
| 5,001,293 | 3/1991 | Nubel et al. | 585/642 |

*Primary Examiner*—Curtis R. Davis
*Attorney, Agent, or Firm*—Berman & Aisenberg

[57] ABSTRACT

A hydrocarbon is converted to a higher-molecular-weight hydrocarbon having greater unsaturation in compact and efficient apparatus, which provides for recirculating materials in a continuous process.

20 Claims, 1 Drawing Sheet

U.S. Patent    Nov. 26, 1991    5,068,478
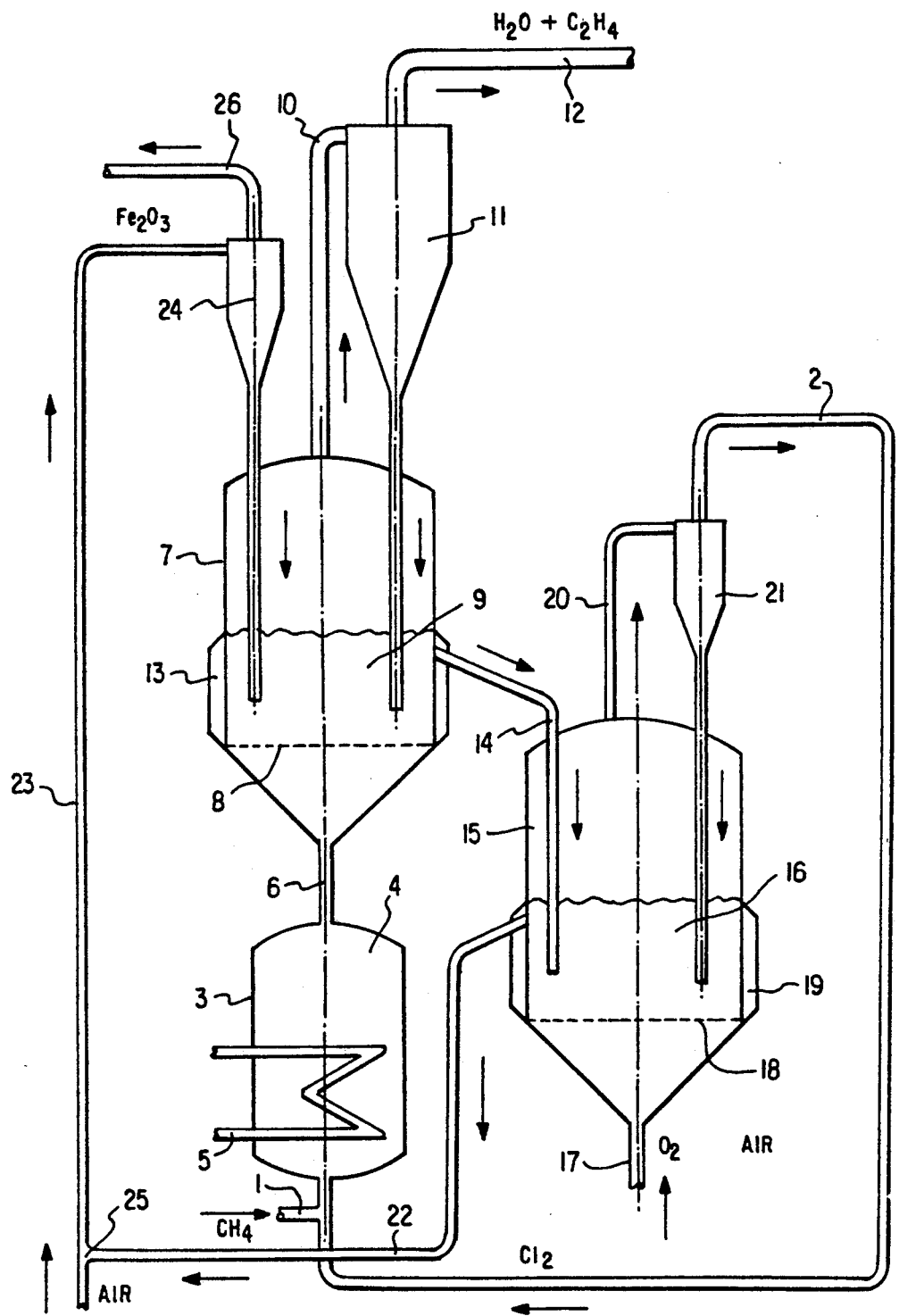

PRODUCING ALKENES AND ALKYNES FROM ALKANES AND ALKENES

FIELD OF THE INVENTION

Alkenes are prepared from alkanes, and alkynes are prepared from alkenes by substantially the same process.

SUMMARY OF THE INVENTION

By reacting an alkyl chloride with a metal oxide in the presence of hydrogen chloride, the alkyl chloride is converted to an alkene having twice the number of carbon atoms of the starting alkyl chloride. Similarly, reacting an alkenyl chloride with a metal oxide in the presence of hydrogen chloride results in the preparation of an alkyne having twice the number of carbon atoms of the starting alkenyl chloride.

Effective and efficient apparatus for conducting the noted conversions is provided by three reactors. The first reactor converts a hydrocarbon and chlorine to a hydrocarbyl chloride and hydrogen chloride; the second converts the hydrocarbyl chloride, the hydrogen chloride and a metal oxide to the corresponding metal chloride, water vapor and a hydrocarbon having higher molecular weight and a higher degree of unsaturation than the starting hydrocarbon. The third reactor converts the metal chloride produced in the second reactor and air or oxygen to the corresponding metal oxide and chlorine. For efficient operation, the metal oxide produced in the third reactor is recirculated to the second reactor, and the chlorine produced in the third reactor is recirculated to the first reactor. The system is both compact and efficient.

BRIEF DESCRIPTION OF THE DRAWINGS

FIG. 1 is a flow diagram with schematic representations of applicable apparatus.

DETAILS

The apparatus and process aspects of this invention are substantially the same whether the starting hydrocarbon is saturated or ethylenically unsaturated. Solely for illustrative purposes, the process is exemplified for the production of ethylene from methane. For that particular process, the following steps are involved:

1) chlorinating methane to form methyl chloride and hydrochloric acid

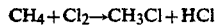    I reacting the methyl chloride and hydrochloric acid formed with ferric oxide to form ethylene, ferric chloride and water vapor

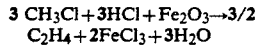    II separating the ethylene and water vapor from the ferric chloride, and oxidizing the ferric chloride with oxygen or air to form ferric oxide and chlorine.

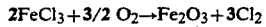    III

In a continuous process the ferric oxide is recirculated.

In this process the starting hydrocarbon, i.e. methane, can be replaced with a different alkane, preferably a lower alkane. When the starting hydrocarbon is an alkane, the produced hydrocarbon is an alkene of higher molecular weight; in fact, the produced alkene has twice the number of carbon atoms possessed by the starting alkane. Similarly, the starting hydrocarbon can be an ethylenically-unsaturated hydrocarbon, preferably a lower alkene. When the starting material is such a hydrocarbon, the hydrocarbon product is an alkyne having twice the number of carbon atoms as the starting hydrocarbon.

When the starting hydrocarbon is ethane, the produced hydrocarbon is butene. The starting hydrocarbon preferably has no more than four carbon atoms.

The chlorination of alkanes and alkenes often leads to a mixture of products. In the case of methane, e.g., pure methylchloride is not usually obtained; the reaction product can include the dichloride, trichloride and even the tetrachloride. By controlling reaction conditions in a known manner, higher degrees of chlorination are minimized. In any event, undesired byproducts are readily and conventionally separated out.

References throughout the disclosure and process claims to alkane and alkene chlorides are to respective monochlorides.

In the preceding illustration ferric oxide is used; this can be replaced by numerous other metal oxides, such as zinc oxide and copper oxide.

To illustrate the invention further, reference is made to the drawings, which primarily illustrate the apparatus aspect of the invention.

Following the previously-noted reactions, methane from line 1 is mixed with chlorine coming through line 2 and introduced into reactor 3 containing heat exchanger means (heater-cooler) 5, reacting in space 4 to form methyl chloride and hydrochloric acid. The mixture of produced gases passes through line 6 to reactor 7 through porous plate 8 into fluidized bed 9, containing ferric oxide, and reacts therein to form ferric chloride, ethylene and water vapor.

The resulting gasses, laden with dust, flow through line 10 to cyclone 11, returning dust through the cyclone downcomer and delivering clean gas (containing ethylene and water vapor) through line 12.

Heat exchange media 13 are used to control the reaction temperature.

Ferric chloride formed in fluidized bed 9 is conducted through line 14 to reactor 15 into fluidized bed 16.

Air or oxygen flows through line 17 to reactor 15 through porous plate 18, reacting with ferric chloride to form ferric oxide and chlorine. The produced dust-laden chlorine flows through line 20 to cyclone 21, returning dust through the cyclone downcomer to fluidized bed 16. Dust-free chlorine exits through line 2.

Heat exchange media 19 are used to control the reaction temperature. Ferric oxide formed in fluid bed 16 flows through line 22 to air lift 25, flowing upwards through line 23 to cyclone 24, from which dust-free air escapes through line 26 and ferric oxide flows through the cyclone downcomer to fluidized bed 9.

Temperatures of the three reactors can vary widely, depending on the hydrocarbon and hydrocarbyl chloride being reacted. For methane conversion, the temperature of reactor 3 is preferably between 350° C. and 400° C., while the temperature in reactors 7 and 15, when using ferric oxide, should be arround 300° C. to prevent excessive volatilization of ferric chloride.

When using other hydrocarbons (alkanes and alkenes) and other metal oxides, the temperature will be dictated by the thermodynamic properties of each reaction, and is readily ascertainable by anyone of at least ordinary skill in the art.

Dimerization of ethylene is minimized by recirculating an excess of ferric oxide and reducing the temperature of reactor 7. Since all reactions are exothermic, care must be taken to provide sufficient heat transfer area in each reactor.

To insure that no organic chlorinated products remain in the produced, e.g. ethylene, gas, multiple-bed fluidizers can be used to advantage. The same applies to the chlorine fluidizer, in which upper beds can operate at a lower temperature, condensing any metal chloride that escapes oxidation.

The respective fluidized beds (when employed) are prepared conventionally from appropriate materials, well-known to those skilled in the subject art. Similarly, conventional heat exchangers and temperature control means are employed for each of the reactors.

The invention and its advantages are readily appreciated from the preceding description. Various changes may be made in the process and apparatus without departing from the spirit and scope of the invention or sacrificing its material advantages. The instantly-described process and apparatus are merely preferred embodiments of the invention.

What is claimed is:

1. A process for converting an alkane to a higher molecular weight alkene, which comprises:
   a) chlorinating the alkane to produce the corresponding alkane chloride and hydrochloric acid, and
   b) reacting the obtained alkane chloride and hydrochloric acid with a metal oxide to form a metal chloride, water vapor and an alkene of higher molecular weight than said alkane.
2. A process of claim 1 which further comprises:
   c) separating the alkene and water vapor from the metal chloride and
   d) oxidizing the metal chloride with oxygen and/or air to form the metal oxide and chlorine.
3. A process of claim 2 which comprises recirculating the metal oxide from step (d) in a continuous process.
4. A process of claim 3 which comprises recirculating chlorine from step (d) in a continuous process.
5. A process of claim 2 which comprises conducting steps (b) and (d) in fluidized beds.
6. A process of claim 5 wherein the alkane is a lower alkane.
7. A process of claim 6 wherein the alkane is methane.
8. A process of claim 6 wherein the metal oxide is ferric oxide, zinc oxide or copper oxide.
9. A process of claim 8 wherein the metal oxide is ferric oxide.
10. A process for converting an alkene to a higher molecular weight alkyne, which comprises:
    a) chlorinating the alkene to produce the corresponding alkenyl chloride and hydrochloric acid, and
    b) reacting the obtained alkenyl chloride and hydrochloric acid with a metal oxide to form a metal chloride, water vapor and an alkyne of higher molecular weight than said alkene.
11. A process of claim 10 which further comprises:
    c) separating the alkyne and water vapor from the metal chloride and
    d) oxidizing the metal chloride with oxygen and/or air to form the metal oxide and chlorine.
12. A process of claim 11 which comprises recirculating the metal oxide from step (d) in a continuous process.
13. A process of claim 12 which comprises recirculating chlorine from step (d) in a continuous process.
14. A process of claim 11 which comprises conducting steps (b) and (d) in fluidized beds.
15. A process of claim 14 wherein the alkene is a lower alkene.
16. A process of claim 15 wherein the alkene is ethylene.
17. A process of claim 15 wherein the metal oxide is ferric oxide, zinc oxide or copper oxide.
18. A process of claim 17 wherein the metal oxide is ferric oxide.
19. Apparatus which comprises:
    a) reactor means for converting a hydrocarbon and chlorine to the corresponding hydrocarbyl chloride and hydrogen chloride,
    b) reactor means for converting the hydrocarbyl chloride, the hydrogen chloride, and a metal oxide to a metal chloride, water vapor and a hydrocarbon of higher molecular weight and of a higher degree of unsaturation,
    c) reactor means for converting the produced metal chloride and oxygen or air to the corresponding metal oxide and chlorine,
    d) means to recirculate the produced chlorine to reactor means (a),
    e) means to recirculate produced metal oxide to reactor means (b), and
    f) means to withdraw the higher molecular weight hydrocarbon and water vapor from reactor means (b).
20. Apparatus of claim 19, wherein reactor means (b) and reactor means (c) are fluidized bed reactor means.

* * * * *